(12) United States Patent
Reising et al.

(10) Patent No.: US 9,192,180 B2
(45) Date of Patent: Nov. 24, 2015

(54) NUTRITIONALLY ENHANCED FRACTION FROM RICE BRAN AND METHOD OF LOWERING INSULIN RESISTANCE USING SAME

(76) Inventors: Paul Raymond Reising, Evansville, IN (US); Glenn H. Sullivan, Carmel, IN (US)

( * ) Notice: Subject to any disclaimer, the term of this patent is extended or adjusted under 35 U.S.C. 154(b) by 0 days.

(21) Appl. No.: 13/494,998

(22) Filed: Jun. 13, 2012

(65) Prior Publication Data

US 2012/0251621 A1     Oct. 4, 2012

Related U.S. Application Data

(63) Continuation-in-part of application No. 12/882,202, filed on Sep. 15, 2010.

(51) Int. Cl.

| | | |
|---|---|---|
| *A61K 36/899* | (2006.01) | |
| *A61P 3/00* | (2006.01) | |
| *A23L 1/10* | (2006.01) | |
| *A23L 1/30* | (2006.01) | |
| *A23D 9/00* | (2006.01) | |

(52) U.S. Cl.
CPC ............... *A23L 1/1016* (2013.01); *A23D 9/00* (2013.01); *A23L 1/3002* (2013.01); *A23V 2002/00* (2013.01)

(58) Field of Classification Search
CPC ... A61K 36/899; A61K 36/8962; A61K 9/48; A61K 31/122; A61P 3/00; A61P 3/10; A23L 1/1016; A23L 1/3002; A23D 9/00; A23V 2002/00
USPC .......... 424/750, 94.1, 728, 732, 451; 514/690
See application file for complete search history.

(56) References Cited

U.S. PATENT DOCUMENTS

| | | | |
|---|---|---|---|
| 5,985,344 A | 11/1999 | Cherukuri | |
| 6,126,943 A | 10/2000 | Cheruvanky | |
| 6,303,586 B1 * | 10/2001 | McPeak et al. | 514/54 |
| 6,350,473 B1 | 2/2002 | Cheruvanky | |
| 6,558,714 B2 | 5/2003 | Cheruvanky | |
| 6,733,799 B2 | 5/2004 | Cheruvanky | |
| 6,902,739 B2 | 6/2005 | McPeak | |
| 2008/0038385 A1 | 2/2008 | Cherukuri | |
| 2009/0162514 A1 | 6/2009 | Gingras | |
| 2009/0191308 A1 | 7/2009 | Gingras | |
| 2009/0220666 A1 | 9/2009 | Gingras | |
| 2009/0285919 A1 | 11/2009 | Alberte | |

OTHER PUBLICATIONS

Qureshi, A. A. et al. 2002. Effects of stabilized rice bran, its soluble and fiber fractions on blood glucose and serum lipid parameters in humans with diabetes mellitus Types I and II. J. Nutritional Biochem. 13: 175-187.*

Wu, X. et al. 2004. J. Food Compostion and Analysis. 17: 407-422.*

Xianli Wu et al., in the Journal of Food Composition and Analysis 17 (2004) at pp. 407-422.

Qureshi, A.A. et al, 'Effects of stabilized rice bran, its soluble and fiber fractions, on blood glucose levels and serum lipid parameters in humans with diabetes mellitus Types I and II', Journal of Nutritional Biochemistry (2002)13:175-187.

Lynch, et al, How Does Diabatrol® Work?, White Paper, Jan. 8, 2010, passim.

* cited by examiner

*Primary Examiner* — Hamid R Badr
(74) *Attorney, Agent, or Firm* — McAndrews, Held & Malloy, Ltd.

(57) ABSTRACT

Nutritionally enhanced nutraceutical Hydrophilic and Lipophilic Rice Bran Fractions from rice bran are provided, as well as a method of using the same to reduce Insulin Resistance in animals, especially humans with pre-diabetes and Type 2 diabetes or others with symptoms of Metabolic Syndrome. Provided in various example embodiments are mixtures of elevated levels of nutraceutical compounds, including but not limited to gamma-oryzanol, inositol, ferulic acid, tocotrienols and phytosterols and pharmaceutical and nutritional compositions thereof. Steps are provided including evaluating insulin resistance parameters, initiating therapy including providing therapeutic amounts of Hydrophilic and Lipophilic Rice Bran Fractions from rice bran to treat pre-diabetes and Type 2 diabetes or others with symptoms of Metabolic Syndrome, managing compliance with the therapy, and monitoring and reevaluating the therapy.

20 Claims, 2 Drawing Sheets

(per 100g)

| VITAMINS | | | MINERALS | | |
|---|---|---|---|---|---|
| Vitamin A | 5 | Mcg | Potassium | 1218 | G |
| Vitamin $B_1$ | 3.3 | Mg | Calcium | 600 | Mg |
| Vitamin $B_2$ | 0.42 | Mg | Magnesium | 625 | Mg |
| Vitamin $B_3$ | 64 | Mg | Phosphorus | 1,700 | Mg |
| Vitamin $B_5$ | 40 | Mg | Manganese | 13 | Mg |
| Vitamin $B_6$ | 4.5 | Mg | Iron | 4.5 | Mg |
| Vitamin $B_9$ Folic Acid | 46 | Mcg | Copper | 750 | Mcg |
| Vitamin $B_{12}$ | 2 | Mcg | Zinc | 12 | Mg |
| Vitamin C | 70 | Mg | Chromium | 66 | Mcg |
| Vitamin D | 5 | Mcg | Selenium | 32 | Mcg |
| Vitamin E | 51 | Mg | Molybdenum | 28 | Mcg |
| Vitamin K | 10 | Mcg | ORAC $_{Total}$ | 20,500 | mcMoles TE |
| Tocotrienols (T3) | 10.00 | Mg | | | |
| Biotin | 140 | Mcg | | | |
| Choline | 150 | Mcg | | | |
| Inositol | 149 | Mg | | | |
| γ-Oryzanol | 248 | Mg | | | |
| Phytosterols | | | | | |
| β-Sitosterol | 215 | Mg | | | |
| Stigmasterol | 70 | Mg | | | |
| Campesterol | 115 | Mg | | | |
| Brassicasterol | 15 | Mg | | | |

FIG. 1

NUTRITIONALLY ENHANCED FRACTION FROM RICE BRAN AND METHOD OF LOWERING INSULIN RESISTANCE USING SAME

CROSS-REFERENCE TO RELATED APPLICATIONS

This application claims priority to U.S. patent application Ser. No. 12/882,202, filed on Sep. 15, 2010, which is incorporated herein by reference in its entirety.

FEDERALLY SPONSORED RESEARCH OR DEVELOPMENT

None.

TECHNICAL FIELD

The present invention relates to nutritionally enhanced nutraceutical hydrophilic and lipophilic fractions from rice bran and a method of using the same to reduce Insulin Resistance in animals, especially humans with pre-diabetes and Type 2 diabetes or others with symptoms of Metabolic Syndrome. More particularly, the present invention relates to the mixture of elevated levels of nutraceutical compounds, including but not limited to gamma-oryzanol, inositol, ferulic acid, tocotrienols and phytosterols and pharmaceutical and nutritional compositions thereof, and a method of using the same to reduce insulin resistance.

BACKGROUND

Insulin resistance is a physiological condition where the natural hormone insulin becomes less effective at lowering blood sugars. Depending on physical activity and dietary conditions, blood glucose levels may rise outside the normal range and cause adverse health effects. Fat and muscle cells require insulin to absorb glucose. In a dietary state of energy overabundance, cells internally create a cascading process in which insulin receptors on the cell membrane no longer properly interact with insulin. When these cells fail to respond adequately to circulating insulin, glucose is not adequately absorbed, consequently blood glucose levels rise. For many, long periods of insulin resistance precede clinical Type 2 diabetes. During this latent period of insulin resistance blood glucose may be maintained at near normal levels by overcompensation of insulin. It is widely accepted that the diabetic state greatly increases the risk for cardiovascular disease. This process is a continuum and the prediabetic subject also has increased cardiovascular disease risks and inflammation that is primarily associated with insulin resistance.

Convincing evidence has established that insulin resistance is a pre-diabetic state that can predict incident Type 2 diabetes relatively far into the future. Of the diabetic population in the U.S., 90 to 95% suffer from Type 2 diabetes. According to the American Association of Clinical Endocrinologists, up to 80% of Type 2 diabetics are insulin resistant. Numerous studies have documented the development of insulin resistance as a result of increased intake of dietary fats. In both animals and humans, there is an inverse relationship between fasting plasma triglyceride concentration and insulin sensitivity. This medical research associating triglycerides and insulin resistance has practical applications. A multifaceted diabetic medical nutrition therapy program that simultaneously addresses lipids, triglycerides, and insulin resistance can greatly increase the efficacy of a diabetic management program. Recent clinical studies have shown excellent sensitivity at measuring insulin resistance with a triglyceride/glucose index. Others have observed the connections between oxidative stress indicators and lower antioxidant levels.

Elevated Body Mass Index (BMI) is well associated with and the primary contributor to insulin resistance but the initial events triggering the development of insulin resistance and its causal relations with deregulation of glucose and fatty acids metabolism remain unclear. There is clear evidence that insulin resistance is associated with increased oxidative stress and that oxidative stress is the causal agent for insulin resistance. Oxidative stress also disrupts internal antioxidant mechanisms.

Numerous studies have linked increased oxidative stress to insulin resistance. In diabetics, oxidative stress increased and antioxidant defenses are diminished. In both normal individuals and Type 2 diabetic patients, reduction of oxidative stress improved insulin sensitivity as well as improved Beta-cell function. Most Type 2 diabetics are significantly influenced by insulin resistance. A number of researchers have demonstrated that the activities of pathways for reactive oxygen species (ROS) production and oxidative stress increase in liver, muscle and fat tissue in animals and humans before the onset of insulin resistance. Reducing insulin resistance also offers a protective effect on beta-cells. This is very important for the long-term preservation of insulin secretion. Clinical trials have demonstrated improvement of insulin sensitivity in insulin resistance and diabetic patients treated with antioxidants.

Recent landmark research from M.I.T. and the Harvard Medical School indicates that increased oxidative stress levels are an important trigger and causal agent for insulin resistance in numerous physiological settings and that antioxidants were able to decrease insulin resistance caused by oxidative stress. Other researchers have also found that glycemic control and oxidative stress are seen to be tightly related, and improving glycemic control is associated with a lowering of oxidative stress. Reducing oxidative stress can also improve glycemic control. Antioxidants have been shown to reduce oxidative stress and in turn improve insulin secretion and decrease insulin resistance in diabetics. Accordingly, medical nutrition therapy for humans concerned with diabetes should include decreasing fatty acids and increasing intake of effective antioxidants.

Antioxidants should be administered in an effective manner. Many antioxidants work only in specific chemical reactions within the body. Thus, single antioxidant dosages may overload the body with one antioxidant, and saturate that one chemical reaction, but not address the more complex and holistic oxidative stress problem. Some oxidative stress occurs within the cell with over-production of mitochondrial NADH. Many antioxidants are not able to provide intracellular relief of oxidative stress. Antioxidants have demonstrated the ability to decrease oxidative stress, thus preserving Beta-cell function, increasing insulin sensitivity, protecting vascular cell integrity, and repairing nerves in diabetes damaged organs. Additionally, oxidative stress has been documented to inversely affect mitochondrial activity and oxidative stress has been found to be a relevant negative regulator of insulin secretion. Because of the negative effects of oxidative stress, nutrition experts suggest that daily intake should be at least 3,000 to 5,000 Oxygen Radical Absorbance Capacity ("ORAC") units to have a significant impact on plasma and tissue antioxidant capacity. According to estimates however, the average American consumes only 1,000 to 2,000 ORAC units per day. What is needed therefore is a nutritional supplement that makes up for this deficiency in daily antioxidant intake of ORAC units.

SUMMARY

The present inventors have discovered that the enhanced enzymatic extraction processing of enhanced rice bran hydrophilic and lipophilic fractions yields elevated levels of nutraceutical components that can be administered in such a way as to reduce insulin resistance. These compounds are more bioavailable to humans due to enhanced enzymatic processing.

Rice bran is a nutrient-dense composition derived from the milling of rice. Rice bran is a rich source of protein, fat, carbohydrate and a number of micronutrients such as vitamins, minerals, antioxidants, phytochemicals and phytosterols. The nutritional value of rice bran has been well recognized. Use of rice bran in treatment of a number of human ailments, such as diabetes, coronary diseases, arthritis, and cancer, have been described in the following U.S. Patents and published patent applications including: U.S. Pat. No. 5,985,344, issued Nov. 16, 1999, entitled, "Process for Obtaining Micronutrient Enriched Rice Bran Oil;" U.S. Pat. No. 6,126,943, issued Oct. 3, 2000, and entitled, "Method for Treating Hypercholesterolemia, Hyperlipidemia, and Atherosclerosis;" U.S. Pat. No. 6,303,586 issued Oct. 16, 2001, and entitled "Supportive Therapy for Diabetes, Hyperglycemia and Hypoglycemia;" U.S. Pat. No. 6,350,473, issued Feb. 26, 2002 and entitled "Method for Treating Hypercholesterolemia, Hyperlipidemia, and Atherosclerosis;" U.S. Pat. No. 6,558,714, issued May 6, 2003, and entitled "Method for Treating Hypercholesterolemia, Hyperlipidemia, and Atherosclerosis;" U.S. Pat. No. 6,733,799 issued May 11, 2004, and entitled "Method for Treating Hypercholesterolemia, Hyperlipidemia, and Atherosclerosis;" and U.S. Pat. No. 6,902,739, issued Jun. 7, 2005, and entitled "Method for Treating Joint Inflammation, Pain, and Loss of Mobility," and U.S. Patent Application Publication US 2008/0038385 entitled "Therapeutic uses of an anti-cancer composition derived from rice bran." Additional utilizations of rice bran have been described in U.S. Patent Application Publication US 2009/0285919 entitled "Rice Bran Extracts for Inflammation and Methods of Use Thereof;" U.S. Patent Application Publication US 2009/0220666 entitled "Utilization of Stabilized Bran in High Protein Products;" U.S. Patent Application Publication US 2009/0191308 entitled "Method of Preparing Emulsified Cereal Bran Derivatives;" and U.S. Patent Application Publication US 2009/0162514 entitled "Production of Pasta Using Rice Bran and Rice Flour." Each and every one of the foregoing patents and published patent applications are hereby incorporated herein by reference in their entireties for all that they teach and describe.

The present invention relates to the use of end-products of the process of producing nutritionally enhanced nutraceutical hydrophilic and lipophilic fractions from rice bran, which process is described in U.S. patent application Ser. No. 12/882,202, filed on Sep. 15, 2010, which is incorporated herein by reference in its entirety. Such end-products are available from Diabco Life Sciences LLC under the brand name Nutra-Iso™. It has been discovered that these end-products may be used in a method as described herein to reduce Insulin Resistance in animals, especially humans with pre-diabetes and Type 2 diabetes or others with symptoms of Metabolic Syndrome.

More generally, the inventors have discovered that the mixture of elevated levels of nutraceutical compounds including but not limited to any of gamma-oryzanol, inositol, ferulic acid, tocotrienols and phytosterols and pharmaceutical and nutritional compositions thereof, may be used in a method as described herein to supplement medical nutrition therapy and reduce insulin resistance. These nutraceutical levels may be obtained by a series of enzymatic extractions that have been found to yield significantly more bioavailable levels of these compounds. For example, the inventors have discovered that the Nutra-Iso™ brand nutraceutical hydrophilic and lipophilic fractions have significantly increased bioavailability and increased nutraceutical content that may be used to successfully reduce insulin resistance.

Accordingly, what is described herein is a nutraceutical antioxidant complex specially adapted for the treatment, management, and/or prevention of insulin resistance and other conditions in animals, especially humans. Provided is a composition and method for treating, managing or preventing insulin resistance in animals, especially humans, that employs a safe and effective nutraceutical antioxidant complex, without pro-oxidation activity, while providing a beneficial effect to the blood profile. Also provided is an orally delivered composition useful for treating, managing or preventing insulin resistance in animals, especially humans. Further provided is a nutraceutical antioxidant complex for treating animals, especially humans with insulin resistance.

Also provided are compositions of a nutraceutical antioxidant complex with nutritional fortification to enhance antioxidant synergisms. These compositions may be comprised of dosage units effective to reduce insulin resistance levels, such as about 5-50 mg gamma-oryzanol, 10-200 mg of inositol, 5-50 mg ferulic acid, 2-25 mg tocotrienols, and 20-50 mg phytosterols of these nutraceutical antioxidants per day and a complete complex dosage of 5 to 60 gram per day administered once or twice a day.

In various example embodiments, provided is a unique formulation of antioxidants in combination with hydrophilic and lipophilic fractions that provides approximately two to four times the minimum recommended daily antioxidant intake of ORAC units per day.

In various example embodiments the composition may include a nutraceutical antioxidant complex of plant origin having no pro-oxidation activity, wherein antioxidants include soluble and insoluble polyphenols and phytosterols which can be obtained from the genus *Oryza sativa* or *Oryza glaberrima*.

In various example embodiments the composition may comprise any of gamma-oryzanols, inositol, ferulic acid, tocotrienols or their conjugates, including dimers and oligomers, which are suitable for the treatment, management, or prevention of insulin resistance in animals, especially humans.

The nutraceutical antioxidant complex may be prepared through multiple enzymatic processes that may comprise of the steps of: adding at least three enzymes to the slurry separately and heating the slurry sufficiently to activate the given enzymes. These separate enzymatic processes enhance the nutritional content of rice bran by further extracting soluble and insoluble vitamins, minerals, phytosterols and polyphenols bound to the fiber component in the rice bran.

The present improvements are achieved by utilizing additional enzymes under a range of conditions to convert protein and fiber in the rice bran to less complex fractions that can be isolated from insoluble fractions by screening and centrifuging. This process is described in U.S. patent application Ser. No. 12/882,202, filed on Sep. 15, 2010, which is incorporated herein by reference in its entirety, and that process is referred to herein as the "Enhanced Enzyme Treatment" and includes treating rice bran slurries with certain enzymes in single or multiple process steps to facilitate isolation and inclusion of protein and fiber into the hydrophilic and lipophilic fraction from rice bran. With the inclusion of the protein, fat, and fiber fractions, the yield of the finished product is significantly increased in quantity and improved in nutritional quality. The finished products resulting from the Enhanced Enzyme Treatment process are referred to herein as "the Hydrophilic and Lipophilic Rice Bran Fractions." Examples of the Hydrophilic and Lipophilic Rice Bran Fractions include Nutra-Iso™ brand products available from Diabco Life Sciences LLC. Other aspects of the invention are disclosed herein as discussed in this specification.

BRIEF DESCRIPTION OF THE DRAWINGS

Various aspects of the invention can be better understood with reference to the following figures. In the figures, like reference numerals designate corresponding parts throughout the different views. It will be understood that certain components and details may not appear in the figures to assist in more clearly describing the invention.

FIG. 1 is a chart showing typical analytical data of a complex of The Hydrophilic and Lipophilic Rice Bran Fraction resulting from The Enhanced Enzyme Treatment, according to various example embodiments of the invention.

DETAILED DESCRIPTION

1. Rice Bran Hydrophilic Fraction

Figure 2:
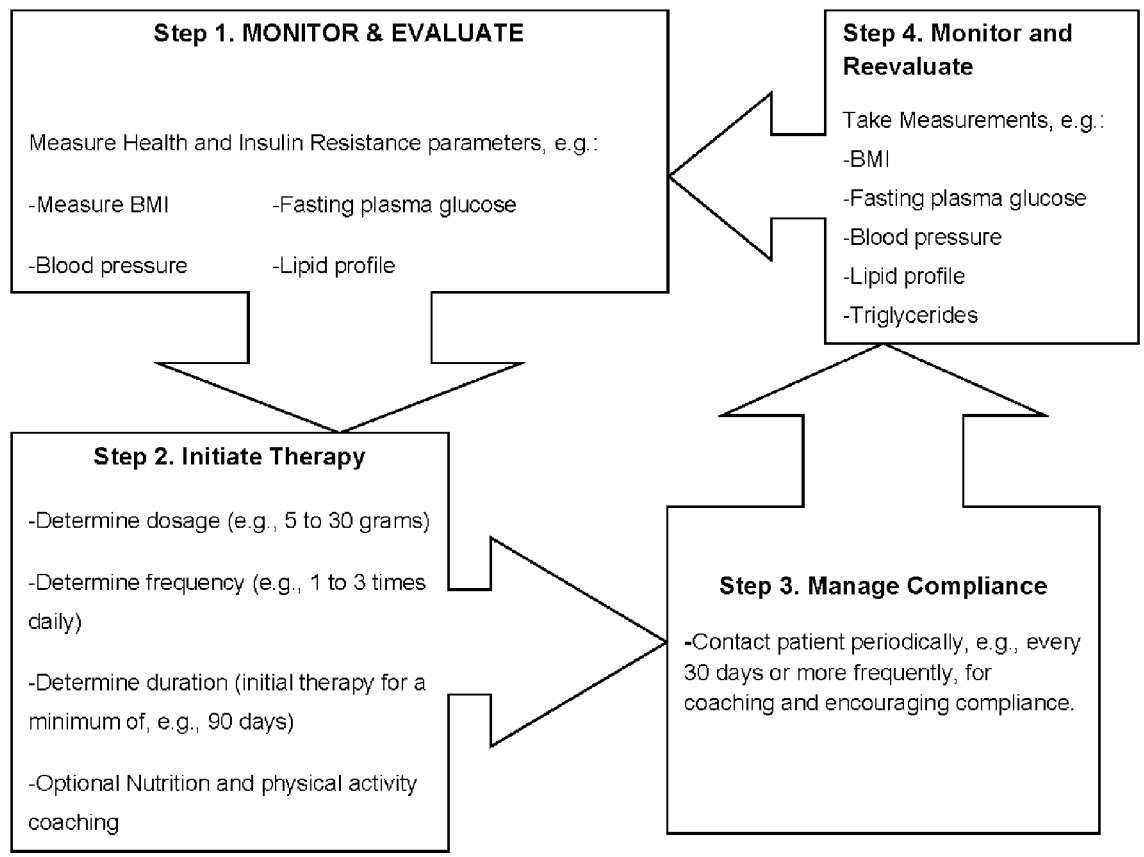
FIG. 2 is flow chart showing example steps of therapeutic processes according to various example embodiments of the invention.

A. Source of Rice Bran Hydrophilic Fraction

The Enhanced Enzyme Treatment process, as defined above, may be completed with at least three potential end-products or fractions. The enzymatic slurry may be designed to extract additional nutrients normally bound too tightly to the bran fiber to become nutritionally available to animals. The rice bran slurry can be separated into hydrophilic and lipophilic fractions. The soluble fraction may be pumped from the slurry and air dried to specific moisture specifications. The resulting Hydrophilic and Lipophilic Rice Bran Fraction is high in niacin and $B_6$ vitamins and also provides significant nutraceutical levels of gamma-oryzanol, ferulic acid and at least four phytosterols. When tested using the ORAC antioxidant analysis method, the Hydrophilic and Lipophilic Rice Bran Fraction has the highest overall $ORAC_{Total}$ level when compared to other rice bran fractions.

2. Rice Bran Fraction of Hydrophilic and Lipophilic Components

A. Source of Rice Bran Fraction of Hydrophilic and Lipophilic components.

When rice bran is subjected to the Enhanced Enzyme Treatment process, as defined above, the end-products can be formulated to create solutions with targeted levels of hydrophilic and lipophilic components. This formulated slurry is not only designed to extract additional nutrients normally bound too tightly to the bran fiber to become nutritionally available to animals, but further to isolate desired hydrophilic and lipophilic components that have been tested for nutraceutical value. This isolated slurry is then air dried to specific moisture specifications. This Hydrophilic and Lipophilic Rice Bran Fraction is more nutritionally robust than the soluble fraction. It is high in niacin, B6, biotin, Choline, copper, magnesium, phosphorus and zinc. This Hydrophilic and Lipophilic Rice Bran Fraction also provides significant nutraceutical levels of inositol and gamma-oryzanol with lesser levels of ferulic acid and phytosterols. When tested using the ORAC antioxidant analysis method, the Hydrophilic and Lipophilic Rice Bran Fraction had significant antioxidant levels.

The analytical method used to analyze the antioxidant composition of the Hydrophilic and Lipophilic Rice Bran Fractions was developed by USDA personnel and further validated, using the methods set forth in Opara E C., Oxidative Stress, Micronutrients, Diabetes Mellitus and its Complications, The Journal of the Royal Society for the Promotion of Health, 122:28-34; and Krauss S, et al., Superoxide-mediated activation of uncoupling protein 2 causes pancreatic β cell dysfunction, Journal of Clinical Investigation, 2003, 112:1831-1843. The analysis of antioxidant capacity of the Hydrophilic and Lipophilic Rice Bran Fractions shown in FIG. 1 was conducted by Brunswick Laboratories, Norton, Mass., utilizing the published methodology noted above. The test was conducted by Y. Kou and supervised and approved by Boxin Ou, PhD.

B. Nutraceutical Significance of Hydrophilic and Lipophilic Components of Interest Scientific research, in both animal and human subjects, generally concludes that there are multiple enzymatic and metabolic actions that play interactive roles in reducing insulin resistance, thereby helping improve blood glucose metabolism, reducing blood glucose and serum insulin levels and reducing the health risks associated with diabetes. Preliminary research concludes that this is also the case with the Hydrophilic and Lipophilic Rice Bran Fractions. The present Hydrophilic and Lipophilic Rice Bran Fractions are thought to interact in several ways to reduce insulin resistance, as described below.

First, the Hydrophilic and Lipophilic Rice Bran Fractions contain very high levels of a number of polyphenols. These polyphenols have significantly higher antioxidant capacity than traditional supplemental vitamins (Vitamin E, C, etc.) In particular, the complex of the invention is high in natural tocotrienols, ferulic acid, gamma-oryzanols, inositol and several phytosterols. These antioxidants, in combination with over 80 additional natural antioxidants provide a nutraceutical foundation for decreasing insulin resistance.

Second, independent laboratory analyses have documented the high natural antioxidant levels found in the Hydrophilic and Lipophilic Rice Bran Fractions, as noted in Brunswick Lab ORAC Test Values, 2012, shown in FIG. 1. Vitamin E is known to have eight homologues that are active in glucose metabolism, four each of tocopherols and tocotrienols. The primary bioactive function of the tocotrienol complex is its capacity as an antioxidant in improved cellular function and protection of the lipid cell membrane, thereby promoting healthy cellular function and more balanced blood glucose metabolism. Results indicate that α-tocotrienol, which is contained in the Hydrophilic and Lipophilic Rice Bran Fractions, may be at least 3-fold more efficient as a scavenger of peroxyl radicals than conventional vitamin E (α-tocopherol). The Hydrophilic and Lipophilic Rice Bran Fractions contain significant levels of tocotrienols. In addition, these tocotrienols have been scientifically documented to lower total cholesterol and LDL cholesterol in blood plasma. Studies suggest that this may be accomplished by inhibiting the activity of the enzyme HMG-CoA which is responsible for cholesterol synthesis in the liver. Micromolar amounts of tocotrienol, but not tocopherol, have been shown to suppress the activity of HMG-CoA. These findings provide insight into how lipid metabolism modification associated with the Hydrophilic and Lipophilic Rice Bran Fractions affect blood glucose metabolism.

Third, the Hydrophilic and Lipophilic Rice Bran Fractions contain very high levels of natural gamma-oryzanols. Scientific studies have confirmed that oryzanol is a natural antioxidant superior to tocopherols. The biologically active portion of gamma-oryzanol is ferulic acid. Just recently in animal studies, ferulic acid significantly decreased the levels of glycogen in the liver and skeletal muscle along with diminishing the activities of hepatic glucose-6-phosphate dehydrogenase, catalase and peroxidase in when compared with controls. In addition, gamma-oryzanol has been shown to affect bile acid secretion and fecal excretion of cholesterol.

3. Nutritional and Nutraceutical Complex of the Hydrophilic and Lipophilic Rice Bran Fractions A. Preparation of the Complex The complex of the Hydrophilic and Lipophilic Rice Bran Fractions can be prepared by dry blending a fine powder of the Fractions in specific ratios in a suitable blender as described below and as described in U.S. patent application Ser. No. 12/882,202, filed on Sep. 15, 2010, which is incorporated herein by reference in its entirety.

4. Pharmaceutical and Nutraceutical Formulation of the Complex of the Hydrophilic and Lipophilic Rice Bran Fractions A. Preparation of Formulations Pharmaceutical and nutritional formulations of the Hydrophilic and Lipophilic Rice Bran Fractions may include suitable pharmaceutical and/or nutritional excipient(s) that are suitable for oral administration. Generally, these oral formulations of the invention fall into one of five categories:

1. A solution, suspension or syrup that is ready for oral administration;
2. A dry powder composition that can be combined with water just prior to use, i.e., a reconstitutable composition;
3. A liquid concentrate ready for dilution prior to administration;
4. A tablet ready for oral administration; or
5. A capsule ready for oral administration.

The orally administered vehicle in these formulations normally has no therapeutic activity and is nontoxic, but presents the active constituent to the body tissues in a form appropriate for absorption. Suitable absorption of the complex normally will occur most rapidly and completely when the composition is presented as an aqueous solution. In preparing formulations which are suitable for oral administration, one can use aqueous vehicles, water-miscible vehicles, or non-aqueous vehicles. Water-miscible vehicles are also useful in the formulation of the composition of the Hydrophilic and Lipophilic Rice Bran Fractions. Another useful formulation is a reconstitutable composition that may be a sterile solid packaged in a dry form. Additional substances may be included in the compositions of the Hydrophilic and Lipophilic Rice Bran Fractions to improve or safeguard the quality of the composition. An added substance may affect solubility, provide for patient comfort, enhance the chemical stability, or protect preparation against the growth of microorganisms. The composition may also include an appropriate solubilizer, or substances that act as antioxidants, and a preservative to prevent the growth of microorganisms. These substances may be present in an amount appropriate for their function, and should not adversely affect the action of the composition.

Preferred pharmaceutical or nutritional formulations are typically those suitable for oral administration to warm-blooded animals. The compositions herein may contain the complex ingredient alone, or in combination with a pharmaceutically or nutritionally acceptable excipient, in dosage unit forms such as dry powder, tablets, coated tablets, hard or soft gelatin capsules or syrups. These administratable forms can be prepared using known procedures, for example, by conventional mixing, granulating, tablet coating, dissolving or lyophilisation processes. Thus, pharmaceutical or nutritional compositions for oral administration can be obtained by combining the active ingredient with solid carriers, optionally granulating the resulting mixture, and processing the mixture by granulation, if desired or necessary, after the addition of suitable excipients, to give tablets or coated tablet cores. Dyes or pigments can be added to the tablets or coated tablets, for example, to identify or indicate different doses of the active complex ingredient.

Other pharmaceutical or nutritional preparations suitable for oral administration are hard gelatin capsules and also soft gelatin capsules made, for example, from gelatin and a plasticizer such as glycerol or sorbitol. Hard capsules may include the complex containing the Hydrophilic and Lipophilic Rice Bran Fractions in admixture with fillers such as lactose, binders such as starches, and/or lubricants such as talc or magnesium stearate, and if desired, stabilizers. In soft capsules, the Hydrophilic and Lipophilic Rice Bran Fractions are preferably dissolved or suspended in a suitable liquid, such as fatty oil, paraffin oil or a liquid polyethylene glycol, to which a stabilizer can be added.

The Hydrophilic and Lipophilic Rice Bran Fraction complex, when obtained by dry blending process, converts into true complex when formulated in aqueous or alcoholic systems. Alternately, this dry blended material can get converted into an effective complex when administered to primates, especially human.

B. Other Active Ingredients

The formulations of the invention may include added active ingredients other than the Hydrophilic and Lipophilic Rice Bran Fraction complex itself, including by way of example and not limitation:

1. Antioxidants: e.g., Alpha lipoic acid, Coenzyme Q;
2. Minerals and Vitamins synergistic to the antioxidant found in the Hydrophilic and Lipophilic Rice Bran Fractions in their effect on the oxidative stress complex: e.g., Vitamin C, Vitamin E, Selenium, Chromium, and Zinc;
3. Minerals, Vitamins, or other compounds with laboratory or clinical evidence of reducing insulin resistance: e.g., Chromium, Boron, Carnitine;
4. Other Minerals, Vitamins, or other compounds with laboratory or clinical evidence in decreasing cardiovascular disease risk: e.g., Vitamin B3, Vitamin B12, Biotin, Folate, B6;
5. Other Minerals and Vitamins needed for optimum health: e.g., Vitamin B5, Vitamin D, Vitamin K, Calcium, Potassium, and Magnesium;
6. Plant extracts: e.g., American ginseng, Bilberry, *Ginkgo biloba*, Garlic and Onions; and
7. Any other suitable ingredients.

5. Therapeutic Uses

A user, including an animal or person, can use the Hydrophilic and Lipophilic Rice Bran Fractions to reduce insulin resistance as described herein. FIG. 2 shows example steps of therapeutic processes according to various example embodiments of the invention.

Step 1, monitor and evaluate, includes measuring health and insulin resistance parameters. Currently there is no clinically efficient method of effectively and directly measuring insulin resistance. Instead, clinicians look at measurable symptoms relating to insulin resistance to manage and reduce the risks associated with insulin resistance. The American Association of Clinical Endocrinology (AACE) has created a position statement on insulin resistance syndrome that summarizes the effective clinical symptoms associated with insulin resistance. The diagnosis of the insulin resistance syndrome according to AACE is based on clinical judgment in view of various factors and symptoms. For example, following are clinical symptoms endocrinologists use to measure and manage insulin resistance:

1. Triglycerides above 1.7 mmol/l (150 mg/dl);
2. HDL-cholesterol for men less than 1.03 mmol/l (40 mg/dl) and for women less than 1.29 mmol/l (50 mg/dl);
3. Blood pressure above 130/85 mmHg; and
4. Plasma glucose, either fasting of 6.1-6.9 mmol/l (110-125 mg/dl) or 2-hour post-glucose challenge of 7.8-11.1 mmol/l (140-200 mg/dl).

Other factors to be considered in the diagnosis in Step 1 are overweight/obesity (body mass index over 25 kg/m$^2$), a family history of Type 2 diabetes, polycystic ovary syndrome, sedentary lifestyle, advancing age, and ethnic groups particularly susceptible to Type 2 diabetes.

The present therapies may be indicated for humans with pre-diabetic condition fasting glucose levels of 100 to 120 mg/dL along with elevated LDL cholesterol or elevated triglycerides and blood pressure at or above 130/85 mmHg. For the diabetic human, the most serious symptom of elevated blood sugar has already been diagnosed. If the human also has elevated blood pressure (exceeding 130/85 mmHg) and elevated LDL cholesterol or elevated triglycerides, then the human should begin therapy as described below with respect to Step 2 shown in FIG. 2.

Step 2 comprises initiating therapy by using or providing the user with a therapeutic amount of the Hydrophilic and Lipophilic Rice Bran Fractions. In various example embodiments, a dosage range of 5 grams to 30 grams of a combination of the Hydrophilic and Lipophilic Rice Bran Fractions may be administered once, twice or three times daily. Dosage range and frequency may be determined by estimated duration of experiencing insulin resistance, severity of fasting glucose levels, triglyceride levels, overall physical activity and obesity. For pre-diabetic humans, a typical therapy may begin with a 10 to 20 gram dosage of the Hydrophilic and Lipophilic Rice Bran Fractions, twice daily for 90 days. For Type 2 diabetic humans, estimated duration of the diabetic condition, blood sugar, lipid and triglyceride levels may be considered in developing a therapeutic program. When A1c levels exceed 7.2% with elevated lipids and triglycerides, a diabetic human may begin therapy with a 20 to 30 gram dose taken two to three times daily.

As mentioned in the American Association of Clinical Endocrinology (AACE) position statement, ethnicity can also play a role in the aggressiveness of initiating therapy and therapeutic dosage and frequency. African-Americans, Hispanics, Pacific Islanders, and Native American Indians are more susceptible than Caucasians to Type 2 diabetes and thus should begin therapy earlier in symptom progression and with more aggressive overall therapy, i.e., higher dosage and/or greater frequency.

Delivery of the Hydrophilic and Lipophilic Rice Bran Fractions could be in the form of a dry powder, tablets, coated tablets, hard or soft gelatin capsules, syrups, or any other suitable delivery means.

It may also be helpful to prescribe or obtain nutrition and physical activity coaching as part of the therapy or to complement the therapy.

In Step 3 compliance with the therapy is managed. The patient or user may be contacted periodically or regularly, for instance at least every 30 days in certain embodiments. When contacted, the patient or user may be coached to help them continue with the therapy, including encouraging the user to consume the Hydrophilic and Lipophilic Rice Bran Fractions at prescribed intervals and to comply with any nutrition and physical activity programs.

Turning to Step 4, the therapy may be periodically monitored and reevaluated. For instance, at the end of the 90-day or other designated period blood may be drawn for glucose and lipid profile analysis. Blood pressure may also be recorded. If blood glucose and lipid profiles have improved measurably, for instance after A1c levels decreased to 5.7%, then a revised therapy may be initiated. A revised therapy may comprise a preventative or maintenance therapy, such as a single 10 to 20 gram dosage of the Hydrophilic and Lipophilic Rice Bran Fractions taken daily with a meal (preferably breakfast). Such a preventative or maintenance therapy may continue until BMI decreases below 24 and blood sugar and lipid profiles remain within healthy ranges for a long period of time, especially when the human has been in the diabetic state for an extensive period of time. If there is a change in the monitored parameters requiring a different or new therapy, then the process returns to Step 1 and repeats.

In various embodiments, any or all of Steps 1, 2, 3 or 4 might be omitted. For example, while it is not advised, in practice a user might simply obtain some of the Hydrophilic and Lipophilic Rice Bran Fractions and self-administer a therapeutic amount, for instance based on instructions on a product container or in advertising material or even in this patent, and thereby obtain some or all of the benefits described herein.

Based on clinical results applying the methods described herein, the likelihood of measurable decreases in insulin resistance parameters is in the range of 80 to 90 percent.

As will be apparent to persons skilled in the art, modifications and adaptations to the above-described example embodiments of the invention can be made without departing from the spirit and scope of the invention, which is defined only by the following claims.

The invention claimed is:

1. A nutraceutical, comprising: a therapeutic amount of a hydrophilic and lipophilic rice bran fraction prepared by an enzyme treatment, wherein said amount is sufficient to treat Insulin Resistance in a user, and wherein said fraction has a total Oxygen Radical Absorbance Capacity of at least 20,500 micromoles Trolox equivalents per 100 grams of said fraction, and wherein said enzyme treatment comprises the use of a beta-glucanase enzyme, a thermotolerant protease enzyme mix derived from *Carica papaya*, and a thermostable alpha-amylase enzyme.

2. The nutraceutical of claim 1, further comprising: therapeutic amounts of hydrophilic and lipophilic fractions from rice bran sufficient to treat pre-diabetes in a user.

3. The nutraceutical of claim 1, further comprising: therapeutic amounts of hydrophilic and lipophilic fractions from rice bran sufficient to treat Type 2 diabetes in a user.

4. The nutraceutical of claim 1, further comprising: therapeutic amounts of hydrophilic and lipophilic fractions from rice bran sufficient to treat Metabolic Syndrome in a user.

5. The nutraceutical of claim 1, wherein: the therapeutic amounts of hydrophilic and lipophilic fractions from rice bran comprise 5 grams to 30 grams of the hydrophilic and lipophilic fractions from rice bran.

6. The nutraceutical of claim 1, wherein: the therapeutic amounts of hydrophilic and lipophilic fractions from rice bran comprise 10 grams to 20 grams of the hydrophilic and lipophilic fractions from rice bran.

7. The nutraceutical of claim 1, wherein the hydrophilic and lipophilic fractions from rice bran are in a solution, suspension, or syrup, and are ready for oral administration.

8. The nutraceutical of claim 1, wherein the hydrophilic and lipophilic fractions from rice bran are in a dry powder composition adapted to be combined with water prior to administration.

9. The nutraceutical of claim 1, wherein the hydrophilic and lipophilic fractions from rice bran are in a liquid concentrate adapted to be diluted prior to administration.

10. The nutraceutical of claim 1, wherein the hydrophilic and lipophilic fractions from rice bran are in a tablet ready for oral administration.

11. The nutraceutical of claim 1, wherein the hydrophilic and lipophilic fractions from rice bran are in a capsule ready for oral administration.

12. The nutraceutical of claim 1, further comprising two or more of any of the following: Alpha lipoic acid; Coenzyme Q; Vitamin C; Vitamin E; Selenium; Chromium; Zinc; Chromium; Boron; Carnitine; Vitamin B3; Vitamin B12; Biotin; Folate; Vitamin B6; Vitamin B5; Vitamin 0; Vitamin K; Calcium; Potassium; Magnesium; Ginseng; Bilberry; *Ginkgo biloba*; Garlic; Onions.

13. A method of treating Insulin Resistance in a user, comprising the steps of: providing the user with a nutraceutical comprising a therapeutic amount of a hydrophilic and lipophilic rice bran fraction prepared by an enzyme treatment, wherein said amount is sufficient to treat Insulin Resistance in the user, and wherein said fraction has a total Oxygen Radical Absorbance Capacity of at least 20,500 micromoles Trolox equivalents per 100 grams of said fraction, and wherein said enzyme treatment comprises the use of a beta-glucanase enzyme, a thermotolerant protease enzyme mix derived from *Carica papaya*, and a thermostable alpha-amylase enzyme.

14. The method of claim 13, further comprising the step of: providing the user with a nutraceutical comprising therapeutic amounts of hydrophilic and lipophilic fractions from rice bran sufficient to treat pre-diabetes in a user.

15. The method of claim 13, further comprising the step of: providing the user with a nutraceutical comprising therapeutic amounts of hydrophilic and lipophilic fractions from rice bran sufficient to treat Type 2 diabetes in a user.

16. The method of claim 13, further comprising the step of: providing the user with a nutraceutical comprising therapeutic amounts of hydrophilic and lipophilic fractions from rice bran sufficient to treat Metabolic Syndrome in a user.

17. The method of claim 13, wherein: the therapeutic amounts of hydrophilic and lipophilic fractions from rice bran comprise 5 grams to 30 grams of the hydrophilic and lipophilic fractions from rice bran.

18. The method of claim 13, wherein: the therapeutic amounts of hydrophilic and lipophilic fractions from rice bran comprise 10 grams to 20 grams of the hydrophilic and lipophilic fractions from rice bran.

19. The method of claim 13, wherein: the nutraceutical further comprises two or more of any of the following: Alpha lipoic acid; Coenzyme Q; Vitamin C; Vitamin E; Selenium; Chromium; Zinc; Chromium; Boron; Carnitine; Vitamin B3; Vitamin B12; Biotin; Folate; Vitamin B6; Vitamin B5; Vitamin D; Vitamin K; Calcium; Potassium; Magnesium; Ginseng; Bilberry; *Ginkgo biloba*; Garlic; Onions.

20. A method of treating Insulin Resistance in a user, comprising the steps of: the user consuming a nutraceutical comprising a therapeutic amount of a hydrophilic and lipophilic rice bran fraction prepared by an enzyme treatment, wherein said amount is sufficient to treat Insulin Resistance in the user, and wherein said fraction has a total Oxygen Radical Absorbance Capacity of at least 20,500 micromoles Trolox equivalents per 100 grams of said fraction, and wherein said enzyme treatment comprises the use of a beta-glucanase enzyme, a thermotolerant protease enzyme mix derived from *Carica papaya*, and a thermostable alpha-amylase enzyme.

\* \* \* \* \*